(12) United States Patent  
Kato (10) Patent No.: US 10,561,831 B2  
(45) Date of Patent: Feb. 18, 2020

(54) TRANSDERMAL ADMINISTRATION DEVICE PACKAGED BODY

(71) Applicant: TOPPAN PRINTING CO., LTD., Taito-ku (JP)

(72) Inventor: Hiroyuki Kato, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 145 days.

(21) Appl. No.: 15/647,598

(22) Filed: Jul. 12, 2017

(65) Prior Publication Data

US 2017/0304604 A1   Oct. 26, 2017

Related U.S. Application Data

(63) Continuation of application No. PCT/JP2016/050848, filed on Jan. 13, 2016.

(30) Foreign Application Priority Data

Jan. 16, 2015   (JP) .................... 2015-006940

(51) Int. Cl.
*A61M 37/00* (2006.01)
*A61F 13/00* (2006.01)
(Continued)

(52) U.S. Cl.
CPC ..... *A61M 37/0015* (2013.01); *A61F 13/0008* (2013.01); *A61F 13/02* (2013.01);
(Continued)

(58) Field of Classification Search
CPC ........... A61F 13/00076; A61F 13/0008; A61K 9/7038; A61M 5/14248; A61M 37/0015;
(Continued)

(56) References Cited

U.S. PATENT DOCUMENTS 2,974,787 A * 3/1961 Murray ................ A61B 17/205
                                                        206/222
7,789,733 B2    9/2010 Sugimura et al.
(Continued)

FOREIGN PATENT DOCUMENTS

EP    2 868 341 A1    5/2015
JP    58-14375 U      1/1983
(Continued)

OTHER PUBLICATIONS

Extended European Search Report dated May 17, 2018 in Patent Application No. 16737378.6, 10 pages.
(Continued)

*Primary Examiner* — Nathan R Price
*Assistant Examiner* — Anh Bui
(74) *Attorney, Agent, or Firm* — Oblon, McClelland, Maier & Neustadt, L.L.P.

(57) ABSTRACT

A transdermal administration device packaged body includes a transdermal administration device including an administration member housed in a container, the administration member having at least one projection protruding from a first surface of a substrate, and an outer package which houses the transdermal administration device and has a bag form including a front component and a rear component. The front component is positioned on a first surface side of the substrate, the rear component is positioned on a second surface side opposite to the first surface side of the substrate, and the front component has an opening member configured to be pulled open to open the outer package.

20 Claims, 5 Drawing Sheets

(51) Int. Cl.
  *A61F 13/02* (2006.01)
  *A61M 5/142* (2006.01)
  *B65D 75/58* (2006.01)
  *A61B 17/20* (2006.01)

(52) U.S. Cl.
  CPC ......... *A61M 5/14248* (2013.01); *B65D 75/58* (2013.01); *A61B 17/205* (2013.01); *A61M 2037/0023* (2013.01); *A61M 2037/0046* (2013.01); *B81B 2201/055* (2013.01)

(58) Field of Classification Search
  CPC .. A61M 2037/0023; A61M 2037/0046; A61B 17/205
  See application file for complete search history.

(56) References Cited

U.S. PATENT DOCUMENTS

| | | | |
|---|---|---|---|
| 8,292,696 B2 | 10/2012 | Sugimura et al. |
| 8,377,364 B2 | 2/2013 | Shiomitsu et al. |
| 8,876,575 B2 | 11/2014 | Sugimura et al. |
| 9,238,384 B2 | 1/2016 | Shiomitsu et al. |
| 2002/0168401 A1 * | 11/2002 | Kanios | A61F 15/001 424/449 |
| 2008/0274166 A1 | 11/2008 | Sacks et al. |
| 2009/0131887 A1 | 5/2009 | Shiomitsu et al. |
| 2014/0034536 A1 | 2/2014 | Reinhardt et al. |
| 2014/0243788 A1 | 8/2014 | Cantor et al. |
| 2015/0335870 A1 | 11/2015 | Quan et al. |

FOREIGN PATENT DOCUMENTS

| | | | |
|---|---|---|---|
| JP | 2003-52740 A | | 2/2003 |
| JP | 2003052740 A | * | 2/2003 |
| JP | 2008-114880 A | | 5/2008 |
| JP | 2008114880 A | * | 5/2008 |
| JP | 2008-543359 A | | 12/2008 |
| WO | WO 02/090210 A1 | | 11/2002 |
| WO | WO 2008/004597 A1 | | 1/2008 |
| WO | WO 2008/013282 A1 | | 1/2008 |
| WO | WO 2014/003002 A1 | | 1/2014 |

OTHER PUBLICATIONS

International Search Report dated Mar. 22, 2016 in PCT/JP2016/050848, filed Jan. 13, 2016.

* cited by examiner

TRANSDERMAL ADMINISTRATION DEVICE PACKAGED BODY

CROSS-REFERENCE TO RELATED APPLICATIONS

The present application is a continuation of International Application No. PCT/JP2016/050848, filed Jan. 13, 2016, which is based upon and claims the benefits of priority to Japanese Application No. 2015-006940, filed Jan. 16, 2015. The entire contents of these applications are incorporated herein by reference.

BACKGROUND OF THE INVENTION

Field of the Invention

The present invention relates to a transdermal administration device packaged body that includes a transdermal administration device used for drug administration.

Discussion of the Background

Use of transdermal administration devices having an administration part such as a microneedle is known as a method for administering a drug into the body via the skin. The microneedle includes a plurality of needle-shaped projections formed on the surface of a substrate (for example, see WO 2008/013282 and WO 2008/004597). In addition to the microneedle, the transdermal administration device further includes an adhesive sheet for affixing the microneedle to the skin, a cover that protects the microneedle, and the like.

In the administration method using a transdermal administration device, the adhesive sheet is affixed to the skin, and the substrate of the microneedle is pressed against the skin so that the projections puncture the skin to create holes, through which a drug is delivered into the skin.

SUMMARY OF THE INVENTION

According to an aspect of the present invention, a transdermal administration device packaged body includes a transdermal administration device including an administration member housed in a container, the administration member having at least one projection protruding from a first surface of a substrate, and an outer package which houses the transdermal administration device and has a bag form including a front component and a rear component. The front component is positioned on a first surface side of the substrate, the rear component is positioned on a second surface side opposite to the first surface side of the substrate, and the front component has an opening member configured to be pulled open to open the outer package.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

The embodiments will now be described with reference to the accompanying drawings, wherein like reference numerals designate corresponding or identical elements throughout the various drawings.

With reference to FIGS. 1 to 6, an embodiment of a transdermal administration device packaged body will be described.

<Overall Configuration of Transdermal Administration Device Packaged Body>

Figure 1:
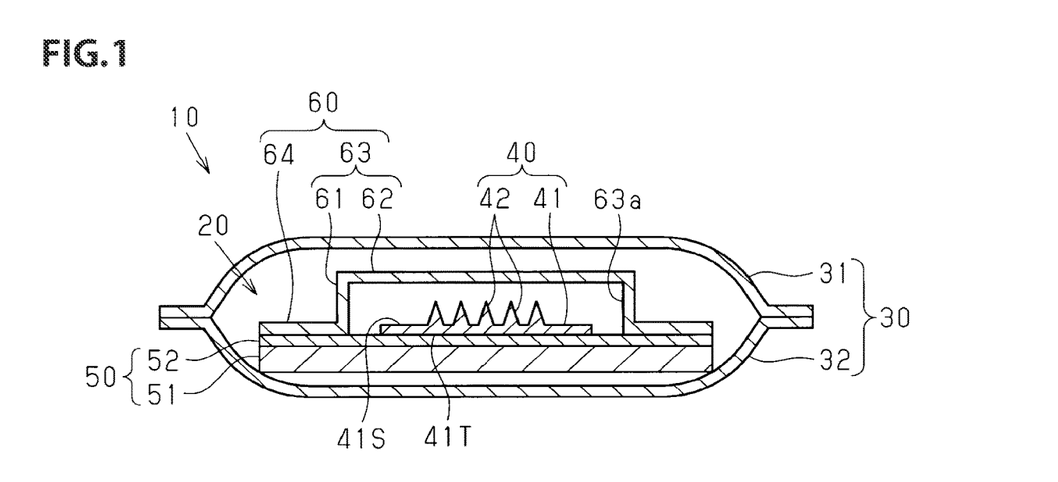
FIG. 1 is a cross-sectional view which illustrates a cross-sectional structure of a transdermal administration device packaged body according to an embodiment, taken along a width direction of the opening member.

As shown in FIG. 1, a transdermal administration device packaged body 10 includes a transdermal administration device 20 and an outer package 30 that houses the transdermal administration device 20. First, a configuration of the transdermal administration device 20 will be described.

The transdermal administration device 20 includes a microneedle 40 which is an example of an administration member, an adhesive sheet 50, and a cover 60.

The microneedle 40 includes a plate-shaped substrate 41 and a projection 42 protruding from the substrate 41. The substrate 41 has a first surface 41S on which the projections 42 are formed and a second surface 41T which is a surface opposite from the first surface 41S. The first surface 41S supports the bases of the projections 42. The outer shape of the substrate 41 as viewed in a direction perpendicular to the first surface 41S is not specifically limited, and may be a circle, oval, or rectangle.

The projection 42 may be a pyramid or cone shape. Further, the projection 42 may be a shape which does not have a pointed tip, for example, a cylinder or prism shape.

Further, the projection 42 may be a shape composed of a combination of two or more three dimensional shapes, for example, a cone stacked on a cylinder. In other words, the projection 42 may be any shape that can pierce the skin. Moreover, the piercing projection 42 may have a narrow portion or shoulder, or a groove or hole formed on the side wall.

The number of projections 42 is not specifically limited, but is one or more. When the microneedle 40 includes a plurality of projections 42, the plurality of projections 42 may be arranged regularly or irregularly on the first surface 41S of the substrate 41. For example, the plurality of projections 42 is arranged in a matrix or concentric pattern.

The adhesive sheet 50 includes a base sheet 51 and an adhesive layer 52 which covers one of two surfaces of the base sheet 51. The adhesive layer 52 is bonded to the second surface 41T of the substrate 41.

The outer shape of the adhesive sheet 50 is larger than the substrate 41 when viewed in the direction perpendicular to the first surface 41S of the substrate 41. In other words, the adhesive layer 52 of the adhesive sheet 50 extends outward from the substrate 41 when viewed in the direction perpendicular to the first surface 41S. The outer shape of the adhesive sheet 50 is not specifically limited, and may be a circle, oval, or rectangle.

The cover 60 is a container having a recess that covers the microneedle 40. The cover 60 includes a main body 63 composed of a tubular member 61 having a tubular shape such as a cylindrical or quadrangular cylindrical shape, and an upper plate 62 having a plate shape that closes one of two ends of the tubular member 61. The inner side surface of the main body 63 defines a housing space 63a that houses the microneedle 40. Further, the cover 60 includes a flange 64 that extends outward from the entire circumference of one of two ends of the tubular member 61, which is located opposite from the end having the upper plate 62. The flange 64 is formed in an annular plate shape.

The main body 63 face the tips of the projection 42 so as to surround the microneedle 40, and the microneedle 40 is disposed in the housing space 63a. That is, the cover 60 and the microneedle 40 are disposed such that one of two surfaces of the upper plate 62 which faces the housing space 63a and the first surface 41S of the substrate 41 face each other.

The outer shape of the tubular member 61 is larger than the outer shape of the substrate 41 and smaller than the outer shape of the adhesive sheet 50 when viewed in the direction perpendicular to the first surface 41S of the substrate 41. One of the surfaces of the flange 64 which is oriented opposite from the upper plate 62 is adhered to the adhesive layer 52 of the adhesive sheet 50 which extends outward from the substrate 41. The outer edge of the adhesive sheet 50 preferably overlaps the outer edge of the flange 64 when viewed in the direction perpendicular to the first surface 41S of the substrate 41.

The main body 63 may be any shape that defines the housing space 63a as a space for housing the microneedle 40, and may be for example a hemisphere shape, which is not composed of separate parts such as the tubular member 61 and the upper plate 62.

In the above configuration, the housing space 63a is closed by the adhesive sheet 50, and the cover 60 and the adhesive sheet 50 serve as a container that houses the microneedle 40.

Next, a configuration of the transdermal administration device packaged body 10 will be described.

The outer package 30 is formed as a sealed bag that houses the transdermal administration device 20. The outer package 30 is made of a soft packaging material, which may be a multi-layered film that contains an aluminum layer. Although the multi-layered film that contains an aluminum layer is opaque, the outer package 30 made of such a multi-layered film has enhanced light blocking properties and gas barrier properties such as water vapor barrier properties, which advantageously enables the quality of the transdermal administration device 20 to be maintained.

The outer package 30 includes a front component 31 and a rear component 32. The front component 31 and the rear component 32 are each formed in a film shape, and the transdermal administration device 20 is housed in a space defined by the front component 31 and the rear component 32.

The front component 31 faces the cover 60 and also faces the tips of the projections 42 and the first surface 41S of the substrate 41 via the cover 60.

The rear component 32 faces the adhesive sheet 50 and also faces the second surface 41T of the substrate 41 via the adhesive sheet 50.

The outer package 30 may be composed of a single film-shaped member. In this case, the front component 31 and the rear component 32 are formed by two facing portions of the single film-shaped member which is double-folded. The front component 31 and the rear component 32 are sealed to each other at three sides, which are the sides other than the folded line. Alternatively, the front component 31 and the rear component 32 may be separate members, and the outer package 30 may be formed by sealing the rims of the front component 31 and the rear component 32 which faces each other.

The outer package 30 may also include an additional member that connects the front component 31 and the rear component 32, and the outer package 30 may be formed by connecting the ends of the front component 31 and the end of the rear component 32 via the additional member.

<Detailed Configuration of Administration Member>

Figure 2:
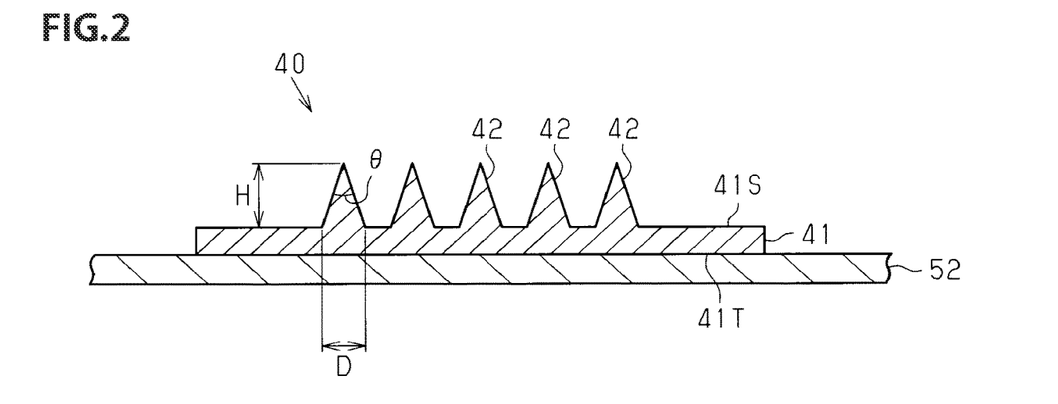
FIG. 2 is a cross-sectional view which illustrates a cross-sectional structure of a microneedle included in a transdermal administration device packaged body according to an embodiment.

With reference to FIG. 2, a detailed configuration of the microneedle 40 will be described, focusing on a configuration of the projection 42.

As shown in FIG. 2, the projection 42 has a length H which is a length from the first surface 41S to the tip of the projection 42 in a direction perpendicular to the first surface 41S of the substrate 41. The length H of the projection 42 is preferably in the range of 10 μm or more and 1000 μm or less, and is determined depending on the depth required for the hole to be punctured by the projection 42 within the above range. When the puncture target is the human skin and the depth of the hole is designed to be in the stratum corneum, the length H is preferably in the range of 10 μm or more and 300 μm or less, more preferably in the range of 30 μm or more and 200 μm or less. When the depth of the hole is designed to penetrate through the stratum corneum and not to reach the nerve, the length H is preferably in the range of 200 μm or more and 700 μm or less, more preferably in the range of 200 μm or more and 500 μm or less, and further more preferably in the range of 200 μm or more and 300 μm or less. When the depth of the hole is designed to reach the dermis, the length H is preferably in the range of 200 μm or more and 500 μm or less. When the depth of the hole is designed to reach the epidermis, the length H is preferably in the range of 200 μm or more and 300 μm or less.

The projection 42 has a width D, which is a maximum length of the projection 42 in a direction parallel with the first surface 41S of the substrate 41. For example, when the projection 42 has a regular quadrangular pyramid or regular quadrangular prism shape, the width D of the projection 42 is a diagonal length of a square defined by the bottom of the projection 42 on the first surface 41S of the substrate 41. Further, when the projection 42 has a cone or cylinder shape, the width D of the projection 42 is a diameter of a circle defined by the bottom of the projection 42. Preferably, the width D of the projection 42 is in the range of 1 μm or more and 300 μm or less.

An aspect ratio A which is a ratio of the length H to the width D of the projection 42 (A=H/D) is preferably in the range of 1 or more and 10 or less.

When the tip of the projection 42 is formed in a pointed shape and the hole is formed to penetrate the stratum corneum by the projection 42, the tip angle θ of the projection 42 is preferably in a range of 5° or more and 30° or less, more preferably in a range of 10° or more and 20° or less. The tip angle θ is a maximum angle made by the tip of the projection 42 in a cross section perpendicular to the first surface 41S of the substrate 41. For example, when the projection 42 has a regular quadrangular pyramid shape, the tip angle θ of the projection 42 is an apex angle of a triangle having a diagonal line of a square defined by the bottom of the projection 42 as a base and the apex of the regular quadrangular pyramid as an apex.

The width D, the aspect ratio A, and the tip angle θ of the projection 42 are determined depending on the volume or the like required for the hole to be formed by the projection 42. When the length H, the width D, the aspect ratio A, and the tip angle θ are within the above ranges, the shape of the projection 42 is in the form suitable for forming a hole into the skin.

<Detailed Configuration of Transdermal Administration Device Packaged Body>

Figure 3:
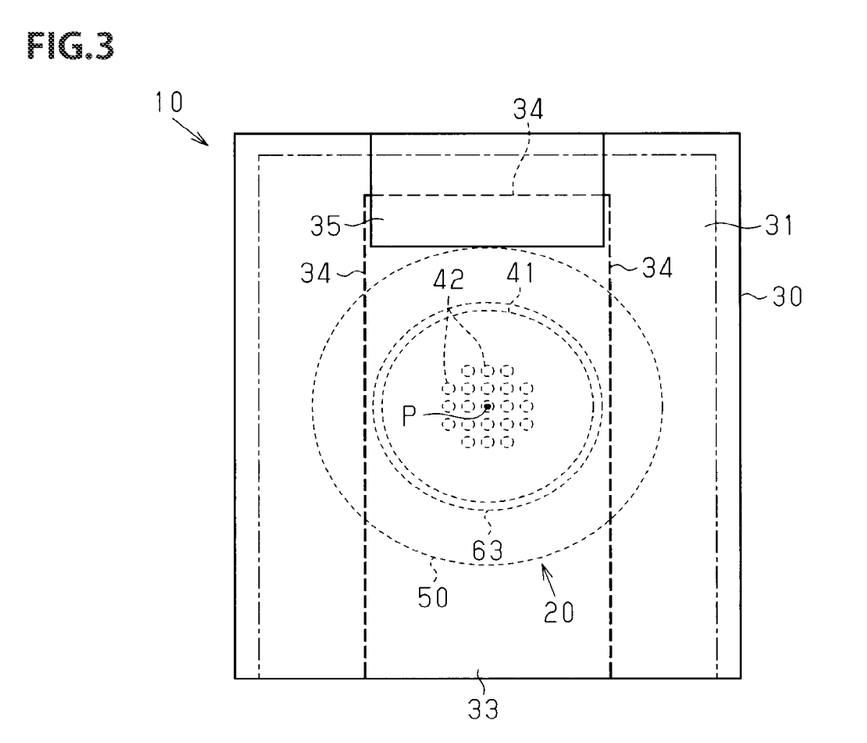
FIG. 3 is a plan view which shows a plan structure of a transdermal administration device packaged body of an embodiment.

With reference to FIG. 3, a detailed configuration of the transdermal administration device packaged body 10 will be described, focusing on a configuration of the outer package 30. FIG. 3 is a view of the transdermal administration device packaged body 10 as viewed from the outside of the outer package 30, and a view of the transdermal administration device packaged body 10 as viewed in a direction perpendicular to the front component 31. In FIG. 3, the thin dotted line represents the transdermal administration device 20 housed in the transdermal administration device packaged body 10, and the dot-and-dash line represents the inner edge of the sealing between the front component 31 and the rear component 32, that is, the edge of the inner space of the outer package 30.

As shown in FIG. 3, the front component 31 includes an opening member 33 which is a strip-shape region extending in one direction. The rear component 32 does not include the opening member 33. The opening member 33 is configured to be separated from a region surrounding the opening member 33 on the front component 31, leaving one end in an extending direction of the opening member 33 unseparated. A direction perpendicular to the extending direction is a width direction of the opening member 33.

In the present embodiment, the opening member 33 is surrounded by a weakened portion 34 except for one end in the extending direction. The weakened portion 34 is a portion of the front component 31 having a shear strength lower than that of the remaining portion. For example, the weakened portion 34 is implemented by perforation. That is, the weakened portion 34 is a portion which is more easily torn by an external force compared with the other portion of the front component 31. When the front component 31 is torn at the weakened portion 34, the opening member 33 except for the aforementioned end is separated from the surrounding region.

The opening member 33 is disposed in the center part of the front component 31 in the width direction when viewed in the direction perpendicular to the front component 31 on the outside of the outer package 30, that is, when the transdermal administration device packaged body 10 is viewed in the direction perpendicular to the first surface 41S of the substrate 41. Further, the opening member 33 overlaps the region where the projections 42 are located on the first surface 41S of the substrate 41 when viewed in the direction perpendicular to the first surface 41S of the substrate 41.

Specifically, the length of the opening member 33 in the extending direction is longer than the entire length of the transdermal administration device 20 when viewed in the direction perpendicular to the first surface 41S of the substrate 41, and the outer edge of the opening member 33 on both ends of the opening member 33 in the extending direction is located outside the outer edge of the transdermal administration device 20.

The length of the opening member 33 in the width direction is shorter than the entire length of the transdermal administration device 20, and longer than the length of the substrate 41, and longer than the length of the main body 63 of the cover 60 when viewed in the direction perpendicular to the first surface 41S of the substrate 41. The outer edge of the opening member 33 on both ends of the opening member 33 in the width direction is located inside the outer edge of the transdermal administration device 20 when viewed in the direction perpendicular to the first surface 41S of the substrate 41, and the opening member 33 overlaps the entire substrate 41.

The length of the opening member 33 in the width direction may be longer than the entire length of the transdermal administration device 20 when viewed in the direction perpendicular to the first surface 41S of the substrate 41, or alternatively, may be shorter than the length of the substrate 41. Further, regardless of the length of the opening member 33 in the width direction, the outer edge of the opening member 33 on at least one end in the width direction may be located outside the outer edge of the transdermal administration device 20 when viewed in the direction perpendicular to the first surface 41S of the substrate 41. The opening member 33 preferably overlaps at least a portion of the transdermal administration device 20 when viewed in the direction perpendicular to the first surface 41S of the substrate 41, and the portion of the transdermal administration device 20 which overlaps the opening member 33 preferably includes a center P of the region where the projections 42 are located on the first surface 41S of the substrate 41.

Even if the outer package 30 has the inner space sufficiently large relative to the size of the transdermal administration device 20 so that the transdermal administration device 20 may be displaced in the outer package 30, the size of the opening member 33 is preferably designed to allow the opening member 33 to overlap the center P at every position where the transdermal administration device 20 may be displaced when viewed in the direction perpendicular to the first surface 41S of the substrate 41. The center P is a center of gravity of the region where the projections 42 are located on the first surface 41S of the substrate 41.

A pull tab 35 is attached to one of the ends of the opening member 33 in the extending direction which has the weakened portion 34. The outer shape of the pull tab 35 may be any shape which can be easily held by a human hand, and may be a rectangular shape or a rounded shape.

Figure 4:
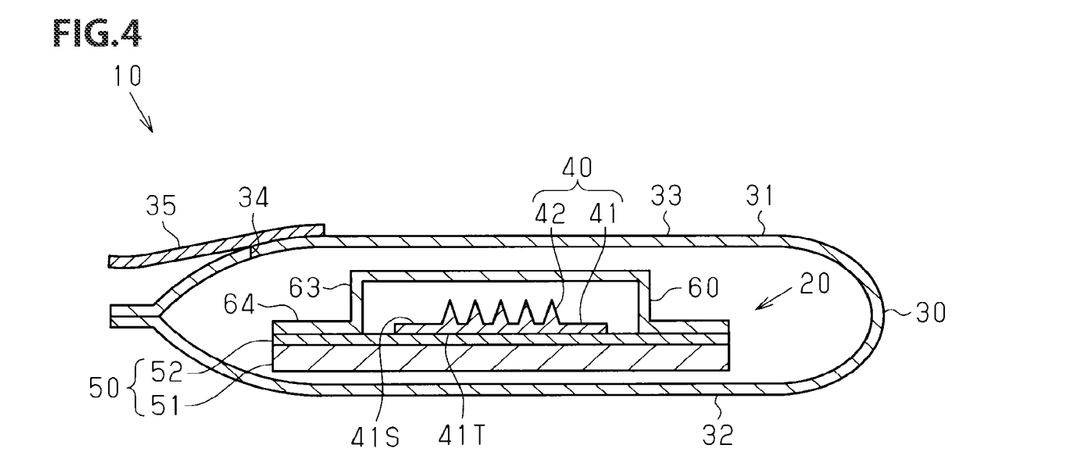
FIG. 4 is a cross-sectional view which illustrates a cross-sectional structure of a transdermal administration device packaged body according to an embodiment, taken along an extending direction of the opening member.

As shown in FIG. 4, the pull tab 35 covers a portion of the opening member 33 and a portion of the front component 31 surrounding the opening member 33, crossing over the weakened portion 34 in the extending direction. The pull tab 35 is fixed only to the opening member 33 via the adhesive layer or the like.

In FIG. 4, of the ends of the pull tab 35 in the extending direction, the end opposite from the end which overlaps the opening member 33 has the outer edge that overlaps the outer edge of the front component 31 which lies under the pull tab 35. However, the pull tab 35 may extend outward or inward in the extending direction relative to the front component 31 which lies under the pull tab 35 when viewed in the direction perpendicular to the first surface 41S of the substrate 41.

<Production Method of Transdermal Administration Device Packaged Body>

A production method of the transdermal administration device packaged body 10 as well as the material and production method of the components of the transdermal administration device 20 will be described.

The microneedle 40 is preferably made of a biocompatible material. Examples of the biocompatible material include metals such as silicon, stainless steel, titanium, and manganese, and resins such as medical grade silicone, polylactic acid, polyglycol acid, polycarbonate, and cyclic olefin copolymer.

Alternatively, the microneedle 40 may be made of a material that dissolves in water contained in the skin. Examples of the material having solubility include a water soluble polymer. Examples of the water soluble polymer include carboxymethyl cellulose (CMC), methylcellulose (MC), hydroxylpropyl cellulose (HPC), hydroxypropyl methylcellulose (HPMC), polyvinyl alcohol (PVA), polyacrylic acid polymer, polyacrylic amide (PAM), polyethylene oxide (PEO), pullulan, and alginate, pectin.

Further, the substrate 41 and the projection 42 may be made of a material having the same composition, or materials having different compositions.

A drug administered by the microneedle 40 is not specifically limited in the kind of drug as long as it is effective when administered into the skin. The drug may be applied on the surface of the projection 42 and delivered into the skin as the projection 42 creates a hole in the skin. Alternatively, when the projection 42 is made of a soluble material as described above, a drug may be contained inside the projection 42 and delivered into the skin as the projection 42 dissolves. Alternatively, when the projection 42 has a groove or hole, a drug may be filled into the groove or hole and may be delivered into the skin as the projection 42 creates a hole in the skin. Further, a liquid drug may be applied on the skin before or after the projection 42 is pierced into the skin so that the drug is delivered into the skin through a hole created by the projection 42. Moreover, a drug may be applied by combinations of these techniques. When the projection 42 is made of a soluble material, a water soluble polymer that constitutes the projection 42 may serve as a drug.

Examples of a drug include various types of proteins, pharmacologically active agents, or cosmetic compositions, which are appropriately selected depending on the purpose.

Examples of a pharmacologically active agent include vaccines such as influenza vaccine, pain relievers for cancer patients, insulin, biologics, gene therapy agents, injections, oral agents, skin application preparations and the like. In transdermal administration using the microneedle 40, a drug is administered into a hole created in the skin. Therefore, transdermal administration using a microneedle 40 can be applied to not only administration of the pharmacologically active agents used in the conventional transdermal administration, but also administration of pharmacologically active agents that requires hypodermic injection. In particular, transdermal administration using the microneedle 40 is suitable for administration of an injection medication such as vaccines for children since it does not cause pain to a patient in administration. Further, transdermal administration using the microneedle 40 is suitable for administration of an oral medication for children who have difficulty in swallowing an oral medication since it does not require a patient to swallow a drug in administration.

Cosmetic compositions are compositions for use as cosmetics or beauty products. Examples of a cosmetic composition include humectants, colorants, fragrance, and physiologically active agents exhibiting cosmetic effects such as improvement effect on wrinkles, acne, stretch marks or the like, and improvement effect on hair loss or the like. When an aromatic material is used as a cosmetic composition, a fragrance can be imparted to the microneedle 40. Accordingly, the transdermal administration device 20 suitable for use as a beauty product can be obtained.

The microneedle 40 can be produced by various known techniques depending on the forming material of the microneedle 40. For example, when the microneedle 40 is made of a resin, the microneedle 40 can be manufactured by injection molding, extrusion molding, imprinting, hot embossing, casting or the like. Further, the microneedle 40 can also be produced by microprocessing techniques such as lithography, wet etching, dry etching, sand blasting, laser processing, and micromachining.

Alternatively, the microneedle 40 may be produced by producing an original plate for the microneedle 40 by the above-mentioned techniques, and producing an intaglio plate having an inverted shape of projections and recesses of the original plate by using a known shape-transfer technique, and filling a forming material for the microneedle 40 into the intaglio plate.

For example, when the microneedle 40 is made of a water soluble polymer, a material solution containing a water soluble polymer and a drug is prepared and supplied into the intaglio plate. The way of supplying the material solution into the intaglio plate may be appropriately selected from known methods taking into consideration the shape or size of the intaglio plate or the like. For example, the material solution can be supplied by methods such as spin coating, use of dispenser, casting, and ink jetting. When the material solution in the intaglio plate is dried and solidified, a molded product provided as the microneedle 40 is formed and removed from the intaglio plate to thereby obtain the microneedle 40.

For example, when the microneedle 40 is made of a thermoplastic resin, the microneedle 40 may be formed by placing a sheet-shaped thermoplastic resin on the intaglio plate and filling the intaglio plate with the thermoplastic resin by thermal imprinting technique.

The adhesive layer 52 of the adhesive sheet 50 is adhered to the second surface 41T of the substrate 41 of the microneedle 40. Then, the cover 60 is placed on the microneedle 40 and the flange 64 is adhered to the adhesive layer 52 to thereby form the transdermal administration device 20.

Materials for the adhesive sheet 50 are not specifically limited, but the base sheet 51 may be formed of a resin sheet made of polyolefin resin such as polyethylene and polypropylene, polyester resin such as nylon and polyethylene terephthalate, or polyvinyl chloride, polyvinylidene chloride, polyvinyl alcohol or the like. Further, the adhesive layer 52 may be formed of silicone adhesive, rubber adhesive, epoxy adhesive, acrylic adhesive or the like.

Materials for the cover 60 are not specifically limited, but may be polyolefin resin such as polyethylene and polypropylene, polyester resin such as nylon and polyethylene terephthalate, or acrylic resin such as polystyrene.

As described above, the outer package 30 is preferably formed of a multi-layered film containing an aluminum layer. For example, the multi-layered film has three layers, that is, an inner surface layer, an aluminum layer, and an outermost layer. The inner surface layer is a layer oriented inside the outer package 30 and is composed of a heat sealable resin such as low density polyethylene (LDPE), medium density polyethylene, ethylene vinyl acetate copolymer (EVA), cast polypropylene (CPP) and the like. The outermost layer is a layer oriented outside the outer package 30 and is composed of a polyester resin such as polyethylene terephthalate, nylon and the like. An aluminum layer is sandwiched between the inner surface layer and the outermost layer. The aluminum layer may be made of an aluminum foil, that is, a rolled aluminum. Alternatively, the aluminum layer may be formed by a vacuum deposition method such as vapor deposition. The multi-layered film may also include an additional layer besides these three layers. For example, a print layer may be disposed between the layers, or may be disposed on the outermost layer. Moreover, these layers may be adhered to each other, for example, via an adhesive layer disposed between the layers.

As described above, when the outer package 30 is formed of a multi-layered film which contains an aluminum layer, the outer package 30 has enhanced light blocking properties and gas barrier properties such as water vapor barrier properties.

Alternatively, the outer package 30 may be formed of a multi-layered film which does not contain an aluminum layer. For example, when the transdermal administration device 20 contained in the outer package 30 is made of a material which is not easily degraded by light or water vapor, the outer package 30 may be formed of a multi-layered film which does not contain an aluminum layer. Alternatively, the outer package 30 may be formed of a multi-layered film which contains a silicon oxide layer or an aluminum oxide layer as a gas barrier layer instead of an aluminum layer. In this case, the silicon oxide layer or aluminum oxide layer may be made by a vacuum deposition method, and examples of the vacuum deposition method include vapor deposition, sputtering and the like.

The layer configuration of the multi-layered film and the materials of the respective layers of the multi-layered film used for producing the outer package 30 are not limited to the aforementioned layer configuration and materials. Further, the outer package 30 may also be formed of a single layer film.

The outer package 30 is first formed into a bag shape by partially sealing the front component 31 and the rear component 32, leaving a portion of the rim unclosed. For example, when the outer shape of the outer package 30 is a rectangular shape, the front component 31 and the rear component 32 are connected at the three of four sides of the outer package 30, and one side of the outer package 30 is left as an opening. Then, the transdermal administration device 20 is inserted into the outer package 30 through this opening with the cover 60 being oriented to the front component 31. The rims of the front component 31 and the rear component 32 at the opening are sealed to each other to seal the bag. Thus, the transdermal administration device packaged body 10 is formed. The front component 31 and the rear component 32 are sealed, for example, by heat sealing. The pull tab 35 may be attached to the opening member 33 before or after the transdermal administration device 20 is inserted into the outer package 30.

Further, in the present embodiment, both the sheet and the film refer to a flexible and thin structure, and the thickness of the structure is not defined by which of the terms is used. Either one of the structure referred as the "sheet" or the structure referred as the "film" may be larger in thickness than the other, or both may have the same thickness.

<Effects>

Figure 5:
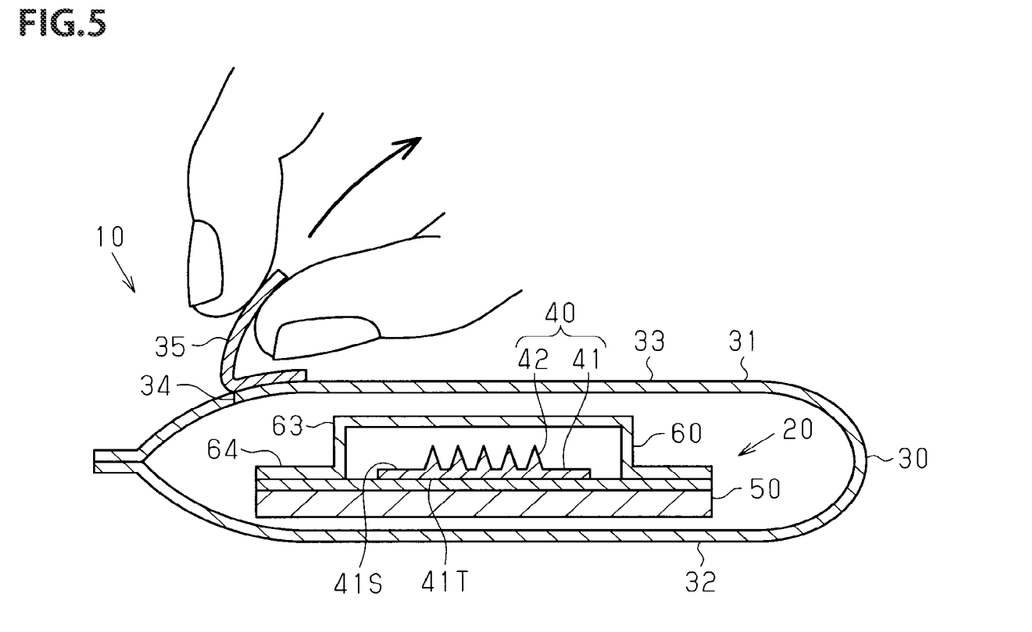
FIG. 5 is a view which illustrates that a transdermal administration device packaged body according to an embodiment is being opened.
Figure 6:
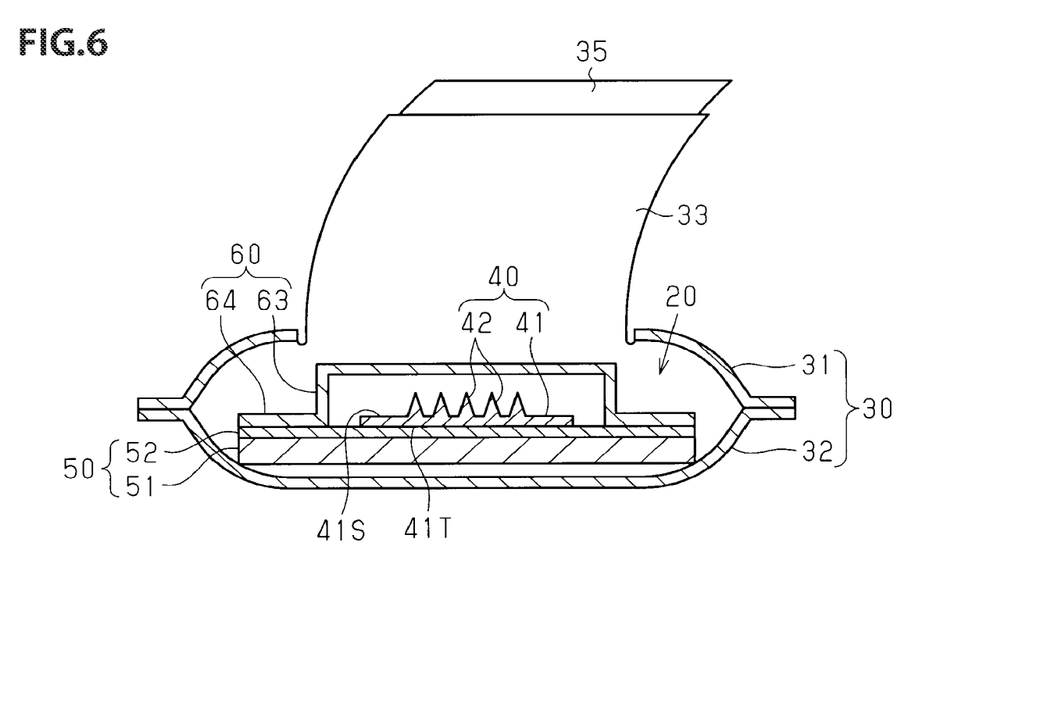
FIG. 6 is a view which illustrates that a transdermal administration device packaged body according to an embodiment has been opened.

With reference to FIGS. 5 and 6, effects of the transdermal administration device packaged body 10 will be described.

As shown in FIG. 5, a user of the transdermal administration device packaged body 10, that is, a person who attempts to take out the transdermal administration device packaged body 10 from the transdermal administration device 20 holds the pull tab 35 with his/her fingers and pulls the pull tab upward. Accordingly, the front component 31 is torn at the weakened portion 34 so that a portion of the opening member 33 is separated from the surrounding region and the opening member 33 is pulled open.

As a result, as shown in FIG. 6, an opening is formed above the cover 60. That is, an opening is formed at a portion of the outer package 30 which faces the first surface 41S of the substrate 41 via the cover 60, in other words, a portion which faces the projection 42 via cover 60. The user inserts his/her fingers into the opening to pick up the transdermal administration device 20 from the opening. After taking out the transdermal administration device 20, the user peels off the cover 60 from the adhesive sheet 50 and then presses the substrate 41 of the microneedle 40 against the skin, to thereby affix the adhesive sheet 50 outside the substrate 41 against the skin. As a result, the projections 42 punctures the skin so that a drug is delivered.

According to the transdermal administration device packaged body 10 of the present embodiment, the outer package 30 is opened by pulling open the opening member 33 which is a portion of the front component 31, thereby allowing the transdermal administration device 20 to be taken out from the opening formed on the front component 31. With this configuration, the aforementioned opening is always formed at a position on the outer package 30 which faces the first surface 41S of the substrate 41. Accordingly, the outer package 30 is prevented from being opened with the tips of the projections 42 oriented downward. When the transdermal administration device packaged body 10 is opened, the tips of the projections 42 are oriented to the opening, and accordingly, the transdermal administration device 20 is taken out with the projection 42 facing the front component as viewed by the user. In this configuration, it is easy for the user to recognize the portion where the projections 42 are formed compared with a configuration in which the opening on the outer package 30 is formed at a position which faces the second surface 41T of the substrate 41 and the transdermal administration device 20 is taken out with the projections 42 facing the rear component as viewed by the user. As a result, an inadvertent force is prevented from being applied to the region adjacent to the projection 42 when the transdermal administration device 20 is taken out.

Further, when the transdermal administration device packaged body 10 is opened, the opening member 33 is separated from the surrounding region to form an opening at the position where the opening member 33 has been located. Therefore, the user does not push the transdermal administration device 20 via the front component 31, particularly, via the opening member 33 during opening of the transdermal administration device packaged body 10. Accordingly, application of force to the region adjacent to the projections 42 which face the front component 31 is prevented. In particular, the area which overlaps the opening member 33 before opening of the transdermal administration device packaged body 10 when viewed in the direction perpendicular to the first surface 41S of the substrate 41 is prevented from being pressed by the user during opening. As a result, in the configuration in which the opening member 33 overlaps the region which includes the center P of the region where the projections 42 are located on the first surface 41S of the substrate 41 before opening when viewed in the direction perpendicular to the first surface 41S of the substrate 41, a force is appropriately prevented from being applied to the region adjacent to the projections 42 by the user pressing the region of the projections 42 via the outer package 30 during opening. Moreover, in the configuration in which the opening member 33 overlaps the entire substrate 41 before opening when viewed in the direction perpendicular to the first surface 41S of the substrate 41, a force is prevented from being applied to the entire region of the substrate 41 during opening, and thus accurately prevented from being applied to the region adjacent to the projections 42.

As described above, in the transdermal administration device packaged body 10 of the present embodiment, the projections 42 are prevented from being deformed during operations such as operations during taking out of the transdermal administration device 20, that is, opening of the transdermal administration device packaged body 10 or taking out of the transdermal administration device 20 through the opening.

In particular, when the outer package 30 is formed of a multi-layered film which contains an aluminum layer, the outer package 30 is opaque. As a result, since the user cannot easily recognize how the transdermal administration device 20 housed in the outer package 30 is oriented before opening of the outer package 30, there has been a risk of an inadvertent force being applied by a user to the region adjacent to the projections 42 during opening of the outer package or taking out of the transdermal administration device through the opening. In contrast to that, according to the transdermal administration device packaged body 10 of the present embodiment, an opening is formed at a position which faces the tips of the projections 42 when a user opens the outer package 30 at the position of the opening member 33 without a need of confirming the orientation of the housed transdermal administration device 20. Accordingly, the transdermal administration device 20 can be taken out with the projections 42 facing the front component. Therefore, when the configuration of the transdermal administration device packaged body 10 according to the present embodiment is applied to the configuration of the outer package 30 formed of a multi-layered film which contains an aluminum layer, the effect of the transdermal administration device packaged body 10 is prominently performed.

In addition, even if the outer package 30 is formed of a multi-layered film which does not contain an aluminum layer, the configuration of the transdermal administration device packaged body 10 according to the present embodiment can also be applied in the similar manner to the configuration described above to achieve a high effect when the multi-layered film is opaque due to having a print layer or the like.

Further, the opening member 33 is formed in a strip-shape, and the length of the opening member 33 in the extending direction is larger than the entire length of the transdermal administration device 20 when viewed in the direction perpendicular to the first surface 41S of the substrate 41. Accordingly, the size of the opening formed by separating the opening member 33 in the extending direction is larger than the entire length of the transdermal administration device 20. As a result, the user can easily take out the transdermal administration device 20 from the opening.

Further, the length of the opening member 33 in the width direction is larger than the length of the main body 63 of the cover 60 when viewed in the direction perpendicular to the first surface 41S of the substrate 41. Accordingly, the main body 63 is prevented from being caught by the edge of the opening during taking out of the transdermal administration device 20. This also helps the user easily take out the transdermal administration device 20.

Further, as described above, according to the transdermal administration device packaged body 10 of the present embodiment, the transdermal administration device 20 is configured to be easily taken out. Accordingly, even if the transdermal administration device packaged body 10 has a small distance between the projection 42 and the upper plate 62 which is a portion of the cover 60 which faces the projection 42, deformation of the projections 42 during taking out of the transdermal administration device 20 can be prevented. Specifically, deformation of the projections 42 by being brought into contact with the cover 60 by a force applying to the region adjacent to the projection 42 can be prevented. As a result, the thickness of the transdermal administration device 20 and thus the thickness of the transdermal administration device packaged body 10 can be reduced. Accordingly, the size of the transdermal administration device 20 and the transdermal administration device packaged body 10 can be reduced, and the cost required for production of the transdermal administration device 20 and the transdermal administration device packaged body 10 can also be reduced.

As described above, according to the transdermal administration device packaged body 10, the following effects can be obtained.

(1) The opening member 33 which is a portion configured to be pulled open on the front component 31 faces the first surface 41S of the substrate 41. Since the outer package 30 is prevented from being opened with the tips of the projections 42 oriented downward and the front component 31 is prevented from being pressed by an inadvertent force, the region where the projections 42 are located is prevented from being pressed during opening of the outer package 30. As a result, since a force is prevented from being applied to the region adjacent to the projections 42 during taking out of the transdermal administration device 20, the projection 42 is prevented from being deformed.

(2) In the configuration in which the opening member 33 overlaps the region which includes the center P of the region where the projections 42 are located on the first surface 41S of the substrate 41 when viewed in the direction perpendicular to the first surface 41S of the substrate 41, the region where the projections 42 are located, in particular, the region adjacent to the center P is prevented from being pressed during opening of the outer package 30. As a result, since a force is appropriately prevented from being applied to the region adjacent to the projections 42 during taking out of the transdermal administration device 20, the projection 42 is prevented from being deformed.

(3) Since the opening member 33 extends in a strip-shape and the length of the opening member 33 in the extending direction is larger than the length of the transdermal administration device 20 when viewed in the direction perpendicular to the first surface 41S of the substrate 41, the transdermal administration device 20 is easily taken out from the opening formed by the opening member 33 being pulled open.

(4) The length of the opening member 33 is larger than the length of the substrate 41 in the width direction when viewed in the direction perpendicular to the first surface 41S of the substrate 41. Accordingly, since the opening formed by the opening member 33 being pulled open has the length larger than the length of the substrate 41 in the width direction, the transdermal administration device 20 is easily taken out compared with the configuration having the opening smaller than the length of the substrate 41.

(5) Since the opening member 33 is defined by the weakened portion 34, the opening member 33 is separated from the surrounding region along the weakened portion 34. Accordingly, since the position where the opening member 33 is separated is determined as the position of the weakened portion 34, the position and size of the opening formed by the opening member 33 being pulled open can be easily determined in advance.

(6) In use of the transdermal administration device packaged body 10, the user can take out the transdermal administration device 20 with the projections 42 facing the front component by opening the outer package 30 at the position of the opening member 33 without a need of confirming the orientation of the housed transdermal administration device 20. Accordingly, the effect of the transdermal administration device packaged body 10 is prominently performed in the configuration having the opaque outer package 30.

In particular, when the outer package 30 is formed of a multi-layered film which includes an aluminum layer, the outer package 30 is opaque. However, the outer package 30 has enhanced light blocking properties and gas barrier properties such as water vapor barrier properties, which enables to advantageously maintain the quality of the transdermal administration device 20. That is, when the outer package 30 in the transdermal administration device packaged body 10 of the present embodiment is formed of the aforementioned multi-layered film, a disadvantage of the outer package 30 being opaque can be counterbalanced by the advantage of the outer package 30 being formed of a multi-layered film which contains an aluminum layer.

Modified Examples

The above embodiment can be implemented with modifications as described below.

The outer package 30 may include a support section which serves as a handle for supporting the transdermal administration device packaged body 10 when the user separates the opening member 33. The support section is provided at a position which does not overlap the transdermal administration device 20 when viewed in the direction perpendicular to the first surface 41S of the substrate 41. For example, a portion of the outer edge of the end of the outer package 30 which is located close to the pull tab 35 may bulge outward so that the bulge portion serves as a support section. Alternatively, a portion of the end of the outer package 30 which is located close to the pull tab 35 may be provided as a handle for the user, and the instruction may be printed thereon to indicate the portion to be held. In this configuration, the user may hold the support section by one hand, and pull the pull tab 35 by the other hand to pull open the opening member 33. Since the holding position of transdermal administration device packaged body 10 is determined in advance so as not to overlap the transdermal administration device 20 during opening, a force is prevented from being applied by the user to the region adjacent to the projections 42 in an accurate manner.

The shape of the opening member 33 is not limited to the strip-shape, and may be, for example, a circular or ellipse shape. The shape and size of the opening member 33 is not limited as long as the opening formed by the opening member 33 being pulled open has the shape and size that allow the transdermal administration device 20 to be taken out. The outer shape of the opening as viewed in the direction perpendicular to the first surface 41S of the substrate 41 is not necessarily larger than the outer shape of the transdermal administration device 20. The shape and size of the opening may be any shape and size that allow the transdermal administration device 20 to be taken out by tilting the transdermal administration device 20 or by expanding the rim of the opening taking advantage of flexibility of the outer package 30.

Regardless of the shape of the opening member 33, the opening member 33 preferably overlaps the center P of the region where the projections 42 are located on the first surface 41S of the substrate 41 when viewed in the direction perpendicular to the first surface 41S of the substrate 41. With this configuration, the center P, that is, the portion where the projections 42 are collected is prevented from being pressed at least during opening. As a result, a force is prevented from being applied to the region adjacent to the projection 42 during opening, for example, compared with the configuration in which the opening position is located on the end of the outer package 30.

The position or configuration of the pull tab 35 is not limited to the above embodiment, and may be any configuration that allows the opening member 33 to be pulled up. The pull tab 35 may or may not be provided. For example, the pull tab may be integrally formed with the opening member 33, or the end of the opening member 33 may be raised and the raised portion may be used as the pull tab.

In the above embodiment, the opening member 33 is configured to be separated from the other portion of the front component 31 except for one end in the extending direction. However, the entire opening member 33 may be configured to be separated from the surrounding region. For example, the entire opening member 33 may be surrounded by the weakened portion 34.

The opening member 33 that can be separated from the other portion of the front component 31 is not necessarily made by defining the opening member 33 by the weakened portion 34. For example, a perforation or slit may be formed on the front component 31 at a position close to the pull tab 35 so that the front component 31 is torn in a linear shape from the perforation or slit by pulling the pull tab 35, thereby allowing the strip-shaped opening member 33 to be separated. Further, a cut tape for cutting the front component 31 may be attached to the inner side surface of the front component 31 so that the front component 31 is cut by pulling the pull tab 35 that is attached to the cut tape.

In the above embodiment, the pull tab 35 is pulled to separate the opening member 33 from the other portion of the front component 31 to thereby open the outer package 30. That is, the opening member 33 is pulled open when a force in the up direction, which is a direction by which the opening member 33 is separated from the front component 31, is applied to the opening member 33. The configuration of the opening member is not limited to the above configuration, and may be any configuration that allows the opening member to be pulled open on the front component 31 to thereby open the outer package 30. For example, the opening member may be configured to be pulled open by a force applied in a lateral direction, which is the extending direction of the front component 31.

Figure 7:
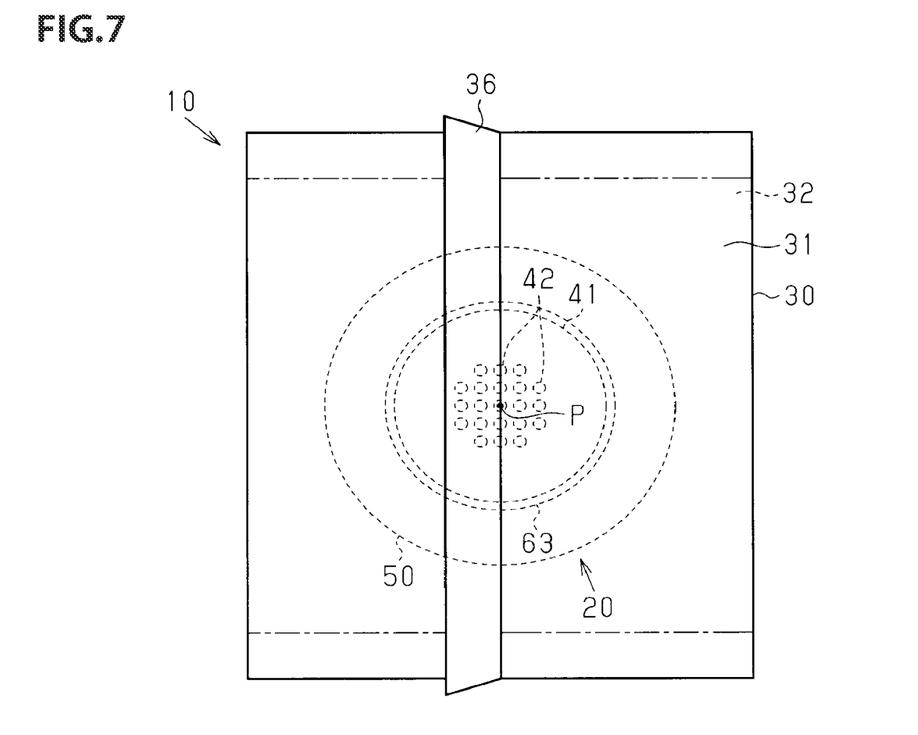
FIG. 7 is a plan view which illustrates a plan structure of the transdermal administration device packaged body of a modified example.

Specifically, as shown in FIG. 7, the outer package 30 may be formed by sealing two opposed sides of a single film-shaped member to form a tubular structure and then sealing the opposed sides on each of two opening ends of the tubular structure. The sealing is performed by heat sealing. This structure is generally called a back-seam bag, or a butt-seam bag. That is, when viewed in the direction perpendicular to the first surface 41S of the substrate 41, the front component 31 and the rear component 32 are sealed to each other at each of the two opposed ends of the outer package 30, and the front component 31 has an opening member 36 which is a sealed portion of the film-shaped member that forms the front component 31 at a position between these two sealed ends. The opening member 36 overlaps the region where the projections 42 are located on the first surface 41S of the substrate 41 when viewed in the direction perpendicular to the first surface 41S of the substrate 41.

Figure 8:
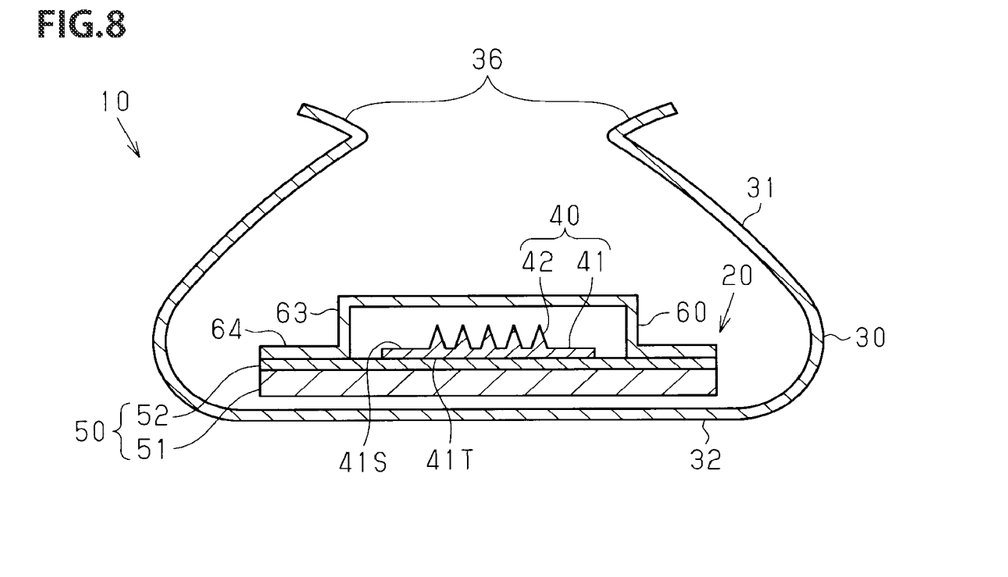
FIG. 8 is a view which illustrates that a transdermal administration device packaged body according to a modified example has been opened.

In opening of the outer package 30, the user holds the regions adjacent to the opening member 36 on the front component 31 on both sides of the opening member 36, and pulls in the direction perpendicular to the extending direction of the opening member 36. Accordingly, the sealing of the opening member 36 is unsealed and the opening member 36 is pulled open. As a result, as shown in FIG. 8, the front component 31 is separated at the opening member 36 to form an opening, through which the transdermal administration device 20 can be taken out.

The outer package 30 may include a print layer, which indicates a caution in opening the outer package 30 to the user, for example, by displaying "Needles this side." Accordingly, a caution in opening the outer package 30 can be given to the user before opening of the outer package 30.

In the above embodiment, the container that houses the microneedle 40 is configured with the adhesive sheet 50 and the cover 60. However, the configuration of the container is not limited the above embodiment, and may be any configuration that houses and protect the microneedle 40.

Figure 9:
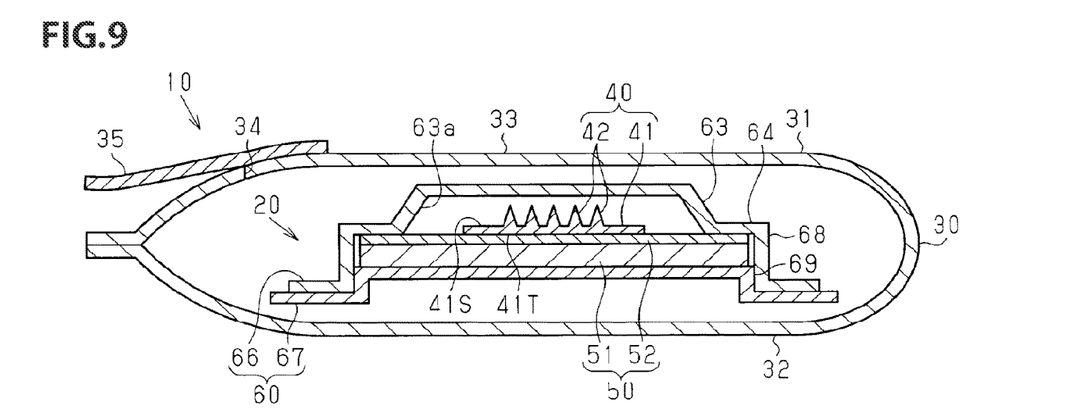
FIG. 9 is a cross-sectional view which illustrates a cross-sectional structure of a transdermal administration device packaged body according to a modified example, taken along an extending direction of the opening member.

For example, as shown in FIG. 9, the cover 60 may be composed of an upper cover 66 and a lower cover 67. The upper cover 66 has a recess that surrounds the microneedle 40, and is disposed to face the first surface 41S of the substrate 41 and the adhesive layer 52 of the adhesive sheet 50. The lower cover 67 supports the base sheet 51 of the adhesive sheet 50. The adhesive sheet 50 is sandwiched between the upper cover 66 and the lower cover 67 around the microneedle 40 so that the structure composed of the microneedle 40 and the adhesive sheet 50 is fixed in position. Further, the upper cover 66 and the lower cover 67 are fitted to each other outside the adhesive sheet 50 when viewed in the direction perpendicular to the first surface 41S of the substrate 41. The configuration for fitting the upper cover 66 and the lower cover 67 to each other is not specifically limited. For example, in the example shown in FIG. 9, the upper cover 66 includes the main body 63 which covers the microneedle 40, the flange 64 which protrudes from the end of the main body 63 and is adhered to the adhesive layer 52, and an annular portion 68 which extends from the flange 64 to the lower cover 67 and surrounds the outer periphery of the adhesive sheet 50. Further, the lower cover 67 includes a raised portion 69 that supports the base sheet 51. When the raised portion 69 is inserted into the annular portion 68, the upper cover 66 and the lower cover 67 are fitted to each other.

Figure 10:
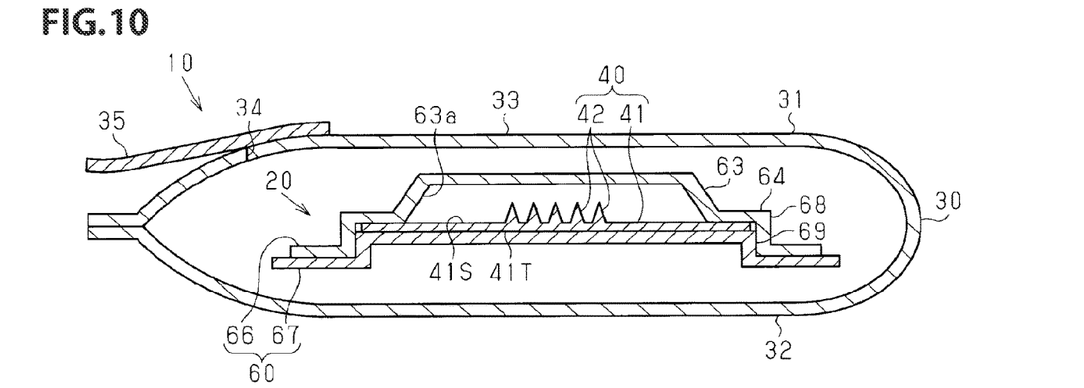
FIG. 10 is a cross-sectional view which illustrates a cross-sectional structure of a transdermal administration device packaged body according to a modified example, taken along an extending direction of the opening member.

Moreover, as shown in FIG. 10, the transdermal administration device 20 may not necessarily include the adhesive sheet 50, and the container may be configured only with the cover 60. In this case, the cover 60 shown in FIG. 9 is preferably used. That is, the upper cover 66 is disposed to face the first surface 41S of the substrate 41, and the lower cover 67 supports the second surface 41T of the substrate 41. The substrate 41 is sandwiched between the upper cover 66 and the lower cover 67 around the projections 42, so that the microneedle 40 is fixed in position. Further, the upper cover 66 and the lower cover 67 are fitted to each other outside the microneedle 40 when viewed in the direction perpendicular to the first surface 41S of the substrate 41.

Figure 11:
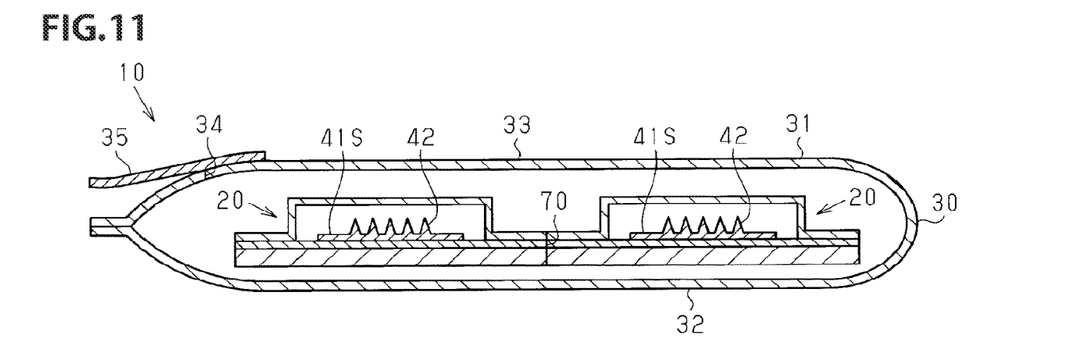
FIG. 11 is a cross-sectional view which illustrates a cross-sectional structure of a transdermal administration device packaged body according to a modified example, taken along an extending direction of the opening member.

As shown in FIG. 11, a plurality of the transdermal administration devices 20 may be housed in the outer package 30 in the transdermal administration device packaged body 10. The plurality of transdermal administration devices 20 is arranged with the projections 42 being oriented in the same direction, that is, the first surfaces 41S of the substrates 41 being oriented in the same direction. The plurality of transdermal administration devices 20 is in a continuous shape, and is configured to be separated along a separation section 70 such as a perforation formed on the adhesive sheet 50 and the cover 60 into the individual transdermal administration devices 20. When the plurality of transdermal administration devices 20 is housed in the outer package 30, the plurality of transdermal administration devices 20 may be arranged in the extending direction of the opening member 33, or in the width direction of the opening member 33, or in the extending direction and the width direction when viewed in the direction perpendicular to the first surface 41S of the substrate 41.

The opening member 33 preferably has a shape and size such that the opening formed by the opening member 33 being pulled open has the shape and size that allow the plurality of transdermal administration devices 20 to be taken out in a continuous form. Further, the opening member 33 preferably overlaps at least one of the transdermal administration devices 20 when viewed in the direction perpendicular to the first surface 41S of the substrate 41, and the portion of the transdermal administration device 20 which overlaps the opening member 33 preferably includes the center P of the region where the projections 42 are located on the first surface 41S of the substrate 41.

The shape of the projection of the administration member is not limited to a needle-shape, that is, the shape extending in a direction perpendicular to the first surface 41S of the substrate 41. The shape of the projection may be a blade shape, that is, a linear shape in which the projection extends in an extending direction along the first surface 41S of the substrate 41 and a distal portion of the projection extends not in the direction perpendicular to the first surface 41S of the substrate 41 but in a direction, for example, extending along the extending direction. For example, the projection may be formed as a triangular prism shape that extends along the extending direction while one of three rectangular side surfaces of the triangular prism is in contact with the substrate 41 and the side of the triangular prism that partitions the other two side surfaces serves as a tip of the projection.

EXAMPLES

The aforementioned transdermal administration device packaged body will be described by using specific examples.
<Fabrication of Transdermal Administration Device>

An original plate for the microneedle was formed from a silicon substrate by micromachining. Thirty six projections were arrayed on a substrate in a 6×6 matrix with a pitch of 1 mm, each having the shape of a regular quadrangular pyramid (length: 150 μm, bottom: 60 μm×60 μm).

The original plate for the microneedle was coated with a nickel film by plating in the thickness of 500 μm. Then, the original plate for the microneedle made of silicon was wet-etched with potassium hydroxide solution of weight percent concentration of 30% which was heated at a temperature of 90° C. to produce an intaglio plate made of nickel.

Next, polycarbonate was disposed on the intaglio plate as a forming material of the microneedle, and filled into the intaglio plate by thermal imprinting. The molded product formed by filling the polycarbonate was removed from the intaglio plate to thereby obtain the microneedle.

An adhesive sheet was disposed on the surface of the microneedle thus obtained where the projections of the substrate were not formed.

A cover was attached on the adhesive sheet to cover the microneedle to thereby obtain the transdermal administration device.
<Production of Transdermal Administration Device Packaged Body>

An outer package was formed of a bag shaped multilayered film made up of an outermost layer made of polyethylene terephthalate, an aluminum layer made of an aluminum foil, and an inner surface layer made of low density polyethylene, and an opening member was formed on the outer package by providing a perforation on one of the surfaces of the bag. The transdermal administration device was inserted into the outer package with the surface on which the opening member facing the projections of the microneedle.

The outer package was sealed by heat sealing to thereby obtain the transdermal administration device packaged body of Example.
<Evaluation of Transdermal Administration Device Packaged Body>

The outer package of the transdermal administration device packaged body was opened by pulling the opening member to take out the transdermal administration device. The projection of the microneedle of the transdermal administration device thus taken out was observed by using a microscope. As a result, deformation of the projection was not observed.

A transdermal administration device may be housed in a sealed outer package for storage before it is used for drug administration. In use of the transdermal administration device, the outer package is opened and the transdermal administration device is taken out from the outer package. At this time, if a large amount of force is applied to the region adjacent to the projection in the transdermal administration device, the projection may be deformed, leading to a decrease in the puncture function of the projection.

An aspect of the present invention is to provide a transdermal administration device packaged body that prevents the projection from being deformed during taking out of the transdermal administration device.

A transdermal administration device packaged body includes: a transdermal administration device; and an outer package of a bag shape that houses the transdermal administration device. The transdermal administration device includes: an administration member which includes a substrate having a first surface and a second surface which is opposite from the first surface, and a projection which protrudes from the first surface; and a container that houses the administration member. The outer package including: a front component and a rear component, the front component facing the first surface of the substrate via the container, the rear component facing the second surface of the substrate via the container, and the front component including an opening member on the front component which is configured to be pulled open to thereby open the outer package.

According to the above configuration, the outer package is opened by pulling open the opening member which is a portion of the front component, thereby allowing the transdermal administration device to be taken out from the opening of the front component 31. In this configuration, the outer package is prevented from being opened with the tips of the projections oriented downward, and the region of the front component adjacent to the opening member is prevented from being pressed by an inadvertent force during opening. Accordingly, the region where the projections are located is prevented from being pressed during opening. As a result, since a force is prevented from being applied to the region adjacent to the projections during taking out of the transdermal administration device, the projection is prevented from being deformed.

In the above transdermal administration device, the opening member may overlap a region where the projections are located on the first surface of the substrate when viewed in a direction perpendicular to the first surface of the substrate.

According to the above configuration, the region where the projections are located is also prevented from being pressed during opening since the opening member configured to be pulled open overlaps a region where the projections are located.

In the above transdermal administration device packaged body, the opening member may extend in a strip-shape, and a length of the opening member in an extending direction of the opening member may be larger than a length of the transdermal administration device when viewed in the direction perpendicular to the first surface of the substrate.

According to the above configuration, the transdermal administration device can be easily taken out since the opening formed by the opening member being pulled open is larger than the length of the transdermal administration device in the extending direction of the opening member.

In the above transdermal administration device packaged body, a length of the opening member in a direction perpendicular to the extending direction of the opening member may be larger than a length of the substrate when viewed in the direction perpendicular to the first surface of the substrate.

According to the above configuration, the transdermal administration device can be easily taken out compared with the configuration having the opening smaller than the length of the substrate since the opening formed by the opening member being pulled open has the length larger than the length of the substrate in a direction perpendicular to the opening member.

In the transdermal administration device packaged body, the front component may include a weakened portion, the weakened portion may be a portion which is more easily torn by an external force compared with a portion of the front component other than the weakened portion, and the opening member may be defined by the weakened portion.

According to the above configuration, the opening member is separated from the surrounding region along the weakened portion. Accordingly, the position and size of the opening formed by the opening member being pulled open can be easily determined in advance since the position where the opening member is separated is determined as the position where the weakened portion is provided.

In the above transdermal administration device packaged body, the outer package may be opaque.

Since the user cannot easily recognize how the transdermal administration device housed in the outer package is oriented before opening of the outer package if the outer package may be opaque, there has been a risk of an inadvertent force being applied by a user to the region adjacent to the projections during opening of the outer package or taking out of the transdermal administration device through the opening. In contrast, according to the above transdermal administration device packaged body, an opening is formed at a position which faces the tips of the projections when a user opens the outer package at the position of the opening member without a need of confirming the orientation of the housed transdermal administration device. Accordingly, the transdermal administration device can be taken out with the tips of the projections being oriented upward. Therefore, when the configuration of the above transdermal administration device packaged body is applied to the configuration having the opaque outer package, the effect of the transdermal administration device packaged body is prominently performed.

In the above transdermal administration device packaged body, the outer package may be formed of a multi-layered film which includes an aluminum layer.

When the outer package is formed of a multi-layered film which includes an aluminum layer, the outer package is opaque. However, the outer package has enhanced light blocking properties and gas barrier properties such as water vapor barrier properties, which enables to advantageously maintain the quality of the transdermal administration device. That is, according to the above configuration, a disadvantage of the outer package being opaque can be counterbalanced by the advantage of the outer package being formed of a multi-layered film which contains an aluminum layer.

According to embodiments of the present invention, the projection is prevented from being deformed during taking out of the transdermal administration device.

REFERENCE SIGNS LIST

10 . . . transdermal administration device packaged body
20 . . . transdermal administration device
30 . . . outer package
31 . . . front component
32 . . . rear component
33, 36 . . . opening member
34 . . . weakened portion
35 . . . pull tab
40 . . . microneedle
41 . . . substrate
41S . . . first surface
41T . . . second surface
42 . . . projection
50 . . . adhesive sheet
51 . . . base sheet
52 . . . adhesive layer
60 . . . cover
61 . . . tubular member
62 . . . upper plate
63 . . . main body
64 . . . flange Obviously, numerous modifications and variations of the present invention are possible in light of the above teachings. It is therefore to be understood that within the scope of the appended claims, the invention may be practiced otherwise than as specifically described herein.

What is claimed is:

1. A transdermal administration device packaged body, comprising:
a transdermal administration device comprising a microneedle and a container housing the microneedle; and
an outer package comprising a front component and a rear component such that the front component and the rear component form a bag form and that the outer package is containing the transdermal administration device,
wherein the microneedle of the transdermal administration device has a substrate and at least one projection protruding from a first surface of the substrate, the outer package is formed such that the front component is positioned on a first surface side of the substrate, that the rear component is positioned on a second surface side opposite to the first surface side of the substrate, and that the front component has an opening member configured to be pulled open and expose the transdermal administration device in the outer package and having a first length larger than the transdermal administration device and a second length perpendicular to the first length and larger than the substrate and smaller than the transdermal administration device, when viewed in a direction perpendicular to the first surface of the substrate.

2. The transdermal administration device packaged body of claim 1, wherein the transdermal administration device is formed such that the container comprises an adhesive sheet holding the microneedle, and a cover covering the microneedle on the adhesive sheet, the opening member is formed to overlap with the transdermal administration device such that the second length is smaller than the adhesive sheet when viewed in the direction perpendicular to the first surface of the substrate.

3. The transdermal administration device packaged body of claim 1, wherein the opening member has a strip form.

4. The transdermal administration device packaged body of claim 2, wherein the opening member has a strip form.

5. The transdermal administration device packaged body of claim 2, wherein the container of the transdermal administration device is formed such that the cover has a main body covering the microneedle on the substrate, and a flange adhered to the adhesive sheet, the opening member has the second length larger than the main body of the cover when viewed in the direction perpendicular to the first surface of the substrate.

6. The transdermal administration device packaged body of claim 4, wherein the container of the transdermal administration device is formed such that the cover has a main body covering the microneedle on the substrate, and a flange adhered to the adhesive sheet, the opening member has the second length larger than the main body of the cover when viewed in the direction perpendicular to the first surface of the substrate.

7. The transdermal administration device packaged body of claim 1, wherein the opening member comprises a weakened portion of the front component which is tearable by a smaller external force as compared to a portion of the front component other than the weakened portion.

8. The transdermal administration device packaged body of claim 2, wherein the opening member comprises a weakened portion of the front component which is tearable by a smaller external force as compared to a portion of the front component other than the weakened portion.

9. The transdermal administration device packaged body of claim 6, wherein the opening member comprises a weakened portion of the front component which is tearable by a smaller external force as compared to a portion of the front component other than the weakened portion.

10. The transdermal administration device packaged body of claim 1, wherein the outer package is opaque.

11. The transdermal administration device packaged body of claim 2, wherein the outer package is opaque.

12. The transdermal administration device packaged body of claim 6, wherein the outer package is opaque.

13. The transdermal administration device packaged body of claim 10, wherein the outer package comprises a multi-layered film which includes an aluminum layer.

14. The transdermal administration device packaged body of claim 11, wherein the outer package comprises a multi-layered film which includes an aluminum layer.

15. The transdermal administration device packaged body of claim 12, wherein the outer package comprises a multi-layered film which includes an aluminum layer.

16. The transdermal administration device packaged body of claim 1, wherein the microneedle has the projection formed in a plurality.

17. The transdermal administration device packaged body of claim 2, wherein the adhesive sheet of the transdermal administration device comprises a base sheet and an adhesive layer formed on the base sheet such that the microneedle is positioned on the adhesive sheet.

18. The transdermal administration device packaged body of claim 1, wherein the outer package comprises a single film folded and sealed to form the front and rear components.

19. The transdermal administration device packaged body of claim 1, wherein the outer package comprises a multi-layered film which includes an aluminum layer.

20. The transdermal administration device packaged body of claim 1, wherein the outer package comprises a multi-layered film comprising an inner heat sealable resin layer, an outer resin layer, and an aluminum layer inter posed between the inner heat sealable resin layer and the outer resin layer.

* * * * *